United States Patent [19]

Meilland

[11] Patent Number: Plant 7,313

[45] Date of Patent: Sep. 4, 1990

[54] ROSE PLANT—MEIGRELOU VARIETY

[75] Inventor: Alain A. Meilland, Antibes, France

[73] Assignee: The Conard-Pyle Company, West Grove, Pa.

[21] Appl. No.: 354,285

[22] Filed: May 19, 1989

[51] Int. Cl.[5] ..... A01H 5/00

[52] U.S. Cl. ..... Plt./24

[58] Field of Search ..... Plt./15, 24

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive long lasting semi-double blossoms. The blossoms are aureolin in coloration. The plant is erect and exhibits vigorous vegetation. The new variety is particularly well suited for growing in a greenhouse for cut flower production. Excellent resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Sweet Promise variety (U.S. Plant Pat. No. 3,095). In the United States the Sweet Promise variety commonly is known as the Sonia variety. The male parent (i.e., the pollen parent) of the new variety was the Kortime variety (nonpatented in the United States). The parentage of the new variety can be summarized as follows:

Sweet Promise × Kortime.

The seeds resulting from the above pollination were sown and small plants were obtained which were physically and biologically different from each other. Selective study resulted in the identification of a single plant of the new variety.

The new variety meets well the needs of the horticultural industry for many uses, and is particularly well suited for growing in a greenhouse for cut flower production.

It was found that the new variety of Floribunda rose plant of the present invention possesses the following combination of characteristics:

(a) abundantly forms attractive long lasting semi-double blossoms which are aureolin in coloration;
(b) forms bronze green adult wood;
(c) exhibits an erect growth habit;
(d) is well adapted for growing in a greenhouse for cut flower production, and
(e) exhibits excellent disease resistance.

The new variety undergoes asexual propagation by a number of routes, including budding, grafting, cuttage, etc. The characteristics of the new variety have been found to be strictly transmissible by such asexual propagation from one generation to another.

The new variety has been named the Meigrelou variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and observed during November while budded on *Rosa indica* understock and growing in greenhouses at Cap d' Antibes, France.

FIG. 11 illustrates a specimen of a floral receptacle showing the pistils (stamens removed);

DETAILED DESCRIPTION

Figures 1, 2, 3, 4, 5, 6, 7, 8, 9, 10, 12, 13, 14, 15, 16:
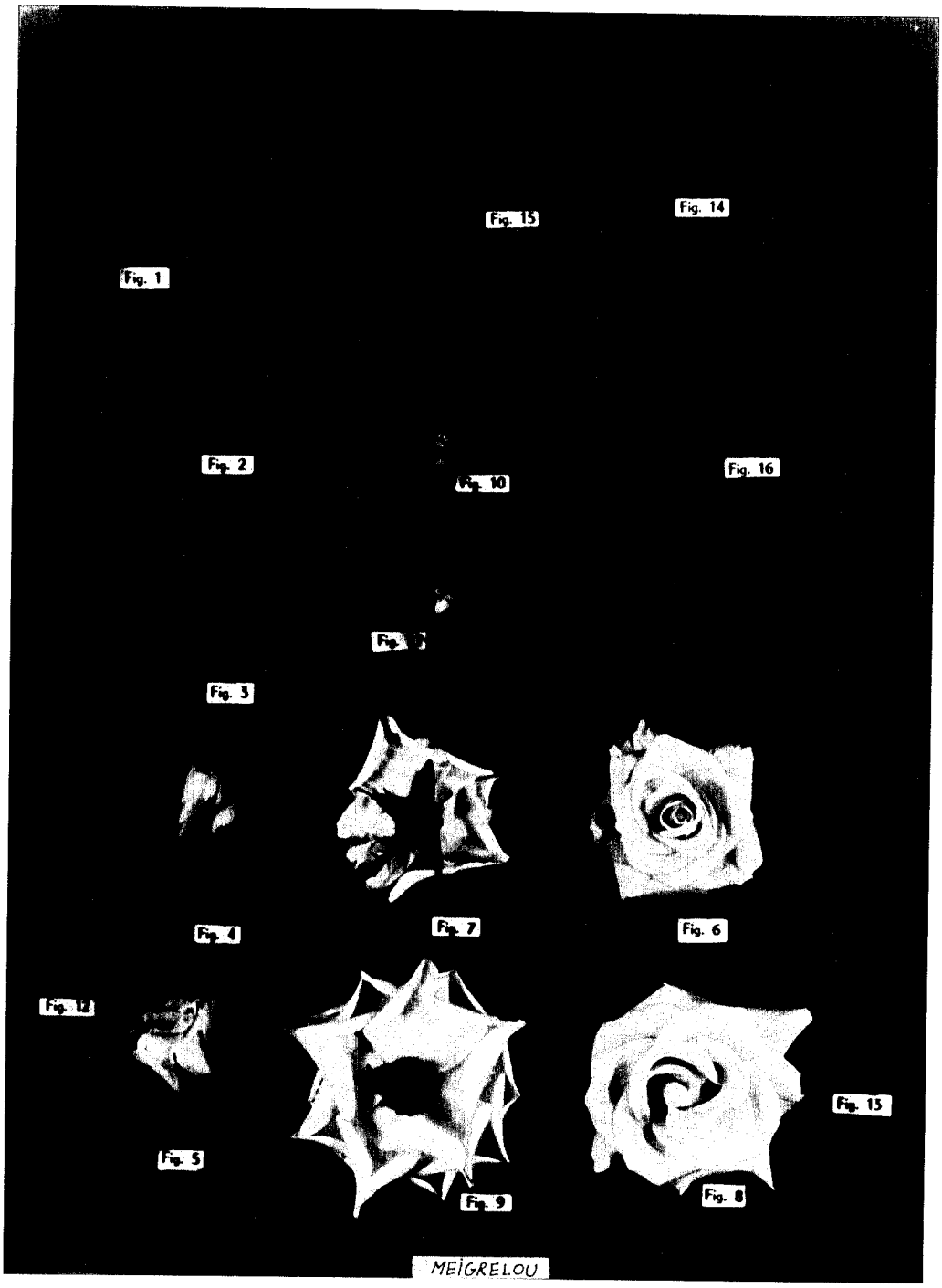
FIG. 1 illustrates a specimen of a young shoot.
FIG. 2 illustrates a specimen of a floral bud before the sepals open.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower prior to petal drop—plan view—obverse.
FIG. 9 illustrates a specimen of a fully open flower prior to petal drop—plan view—reverse.
FIG. 10 illustrates a specimen of a floral receptacle showing the arrangement of the stamens and pistils.
FIG. 12 illustrates a specimen of a young flowering stem (shown upside down)
FIG. 13 illustrates a specimen of an adult main branch (shown upside down)
FIG. 14 illustrates specimens of leaves with three leaflets—upper (right) and under (left) surfaces.
FIG. 15 illustrates specimens of leaves with five leaflets—upper (top) and under (bottom) surfaces.
FIG. 16 illustrates specimens of leaves with seven leaflets—upper (top) and under (bottom) surfaces.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety growing in greenhouses at Cap d' Antibes, France during November while budded on *Rosa indica* understock.

Class: Floribunda.

Plant:

*Height.*—Plants which were pruned to a height of 85 cm. commonly produce floral stems having length of approximately 40 to 60 cm. on average.

*Habit.*—Erect.

Branches:

*Color.*—Young stems: medium green, Yellow-Green Group 146B. Adult wood: bronze green, Yellow-Green Group 146A.

*Thorns.*—Size: small. Quantity: average. Color: pinkish-green on young stems and greenish changing to tan on mature wood.

Leaves:

*Stipules.*—Adnate, pectinate, wide and linear.

*Petioles.*—Upper surface: grooved, reddish brown on young foliage and medium green on adult foliage with more or less glandular edges. Under surface: light green, with numerous prickles.

*Leaflets.*—Number: 3, 5, and 7 (most often). Shape: oval. Serration: single and regular. Texture: consistent. General appearance: foliage is dense and semi-dull. Color (young foliage): Upper surface: lettuce green, Yellow-Green Group 144A, more or less suffused with reddish brown. Under surface: lettuce green, Yellow-Green Group 144A, more or less stained with reddish coloration. Color (adult foliage): Upper surface: dark green, Green Group 137A. Under surface: light green, Green Group 137C.

Inflorescence:

*Number of flowers.*—Usually one per stem, sometimes 2 or 3 per stem.

*Peduncle.*—Light green in coloration, bear numerous glandular prickles, and approximately 5 cm. in length on average.

*Sepals.*—Upper surface: tomentose and greenish in coloration. Under surface: light green in coloration, smooth, and the outside sepals have more or less appendiculated edges ending in a more or less developed leaf-like appendix.

*Buds.*—Shape: conical. Length: approximately 3 to 3.5 cm. on average. Size: medium. Color upon opening: Upper surface: aureolin, Yellow Group 12A turning whitish at the edges. Under surface: medium aureolin, Yellow Group 12B.

*Flower.*—Shape: cuplike and semi-double. Diameter: approximately 6 to 7 cm. on average. Color (when opening begins): Upper surface: aureolin, Yellow Group 12A, turning white on the edges. Under surface: medium aureolin, Yellow Group 12B, turning white on the edges. Color (when blooming): Upper surface: aureolin, Yellow Group 12A. Under surface: medium aureolin, Yellow Group 12B, turning white on the edges. Color (at end of opening): Upper surface: aureolin, Yellow Group 12A. Under surface: aureolin, Yellow Group 12A, and at the center of the petal light aureolin, Yellow Group 12C, turning white at the edge. Fragrance: none. Lasting quality: long. Petal drop: good. Petal number: approximately 18 to 20 on average. Petal texture: consistent. Stamen number: approximately 163 to 170 on average. Anthers: normal, yellowish in coloration, and located at the same level as the pistils. Filaments: bright yellow, regularly disposed around a strip at the base of the floral receptacle, of irregular heights. Pistils: approximately 99 to 106 on average. Stigmas: normal, yellowish in coloration. Styles: greenish base with fuschia tips, pairs are often bonded together, and of irregular heights. Receptacle: light green, smooth, and in longitudinal section in the shape of a funnel.

Development:

*Vegetation.*—Vigorous.

*Blooming.*—Very floriferous.

*Aptitude to be forced.* —Good.

*Resistance to diseases.*—Excellent.

I claim:

1. A new and distinct variety of Floribunda rose plant characterized by the following combination of characteristics:

(a) abundantly forms attractive long lasting semi-double blossoms which are aureolin in coloration,
(b) forms bronze green adult wood,
(c) exhibits an erect growth habit,
(d) is well adapted for growing in a greenhouse for cut flower production, and
(e) exhibits excellent disease resistance;

substantially as herein shown and described.

* * * * *

MEIGRELOU